United States Patent [19]

Reeve

[11] Patent Number: 5,107,020
[45] Date of Patent: Apr. 21, 1992

[54] METHOD FOR PRODUCING PURIFIED TRIMESIC ACID

[75] Inventor: Aubrey C. Reeve, Warrenville, Ill.

[73] Assignee: Amoco Corporation, Chicago, Ill.

[21] Appl. No.: 937,989

[22] Filed: Dec. 4, 1986

[51] Int. Cl.⁵ .......................................... C07C 51/265
[52] U.S. Cl. .................................. 562/416; 562/417; 562/485; 562/486
[58] Field of Search .............. 562/416, 417, 485, 486

[56] References Cited

U.S. PATENT DOCUMENTS

| | | | |
|---|---|---|---|
| 3,007,942 | 11/1961 | Burney et al. | 562/416 X |
| 3,679,740 | 7/1972 | Massie | 562/416 |
| 3,969,405 | 7/1976 | d'Ostrowick et al. | 562/416 |
| 4,330,676 | 5/1982 | Moxham | 562/416 |
| 4,346,232 | 8/1982 | Komatsu et al. | 562/416 |

*Primary Examiner*—Francine Mercer
*Assistant Examiner*—Vera C. Clarke
*Attorney, Agent, or Firm*—James R. Henes; William H. Magidson; Frank J. Sroka

[57] ABSTRACT

A method is disclosed for producing trimesic acid of improved quality and at an improved yield by a process involving the liquid-phase oxidation of mesitylene in a solvent.

9 Claims, No Drawings

METHOD FOR PRODUCING PURIFIED TRIMESIC ACID

BACKGROUND OF THE INVENTION

1. Field of the Invention

This invention relates generally to a method for producing trimesic acid by the liquid-phase oxidation of mesitylene in a solvent, and more particularly concerns a method for producing purified trimesic acid at a greater yield by a process involving the aforesaid liquid-phase oxidation.

2. Discussion of the Prior Art

Trimesic acid is employed as a monomer in the production of specialty polymers and resins. Trimesic acid is also employed in the preparation of germicides, fungicides, plasticizers and cross-linking agents. Obviously, the presence of impurities in trimesic acid can have a serious adverse effect on the physical or chemical properties or performance characteristics of any formulation containing trimesic acid itself or any polymer formed from trimesic acid. In addition, impurities in trimesic acid can adversely affect polymerization processes to which the trimesic acid is subjected. Such impurities in trimesic acid formed by the catalyzed, liquid-phase oxidation of mesitylene are often organic impurities or byproducts formed during the oxidation and inorganic impurities corresponding to metal components of the catalysts employed in the oxidation or formed therefrom. Such impurities often impart undersirable color characteristics to the trimesic acid and its polymerization products.

Thus, minimization and removal of such impurities from trimesic acid are highly desirable. However, the removal of organic and inorganic impurities from aromatic polycarboxylic acids formed by the catalyzed, liquid-phase oxidation of polyalkyl aromatics is typically very difficult, and the removal technique employed depends on the specific aromatic polycarboxylic acid from which the impurities are to be removed and the specific oxidation conditions and catalyst employed to make it. Furthermore, techniques for purifying aromatic polycarboxylic acids are often relatively time consuming and involve relatively complex reaction schemes. Therefore, it is highly desirable to produce trimesic acid under conditions such that the production of impurities and their incorporation in trimesic acid are minimized and the yield of such higher quality trimesic acid is improved.

Thus far, no one has recognized the combination of the weight ratio of solvent-to-mesitylene in the oxidation step, the temperature at which crude trimesic acid is crystallized and separated from the mother liquor, and washing the separated crude trimesic acid with water as a means to effect these desirable goals. For example, Kimura et al., U.S. Pat. No. 4,051,178, disclose a method for producing terephthalic acid by the liquid-phase oxidation of p-xylene in the presence of a cobalt-manganese-bromine catalyst. The only solvent-to-p-xylene volume ratios disclosed are about 3:1, as recited in column 4, lines 28-39 and column 6, lines 16-17. Kimura et al. disclose that, if desired, the terephthalic acid produced may be washed with water or acetic acid.

Kalfadelis et al., U.S. Pat. No. 3,119,860, disclose a method for the oxidation of mesitylene in the presence of a cobalt-manganese-bromine catalyst and the crystallization and recovery of the resulting trimesic acid in which the volume ratio of solvent-to-mesitylene in the oxidation is in the range of 0.3:1 to 3:1 and the crystallized and separated trimesic acid crystals are purified by washing with an acid reaction medium such as substantially anhydrous acetic acid.

Kurtz, U.S. Pat. No. 3,171,856, discloses a process for purifying aromatic carboxylic acids formed by the liquid-phase oxidation of a methyl aromatic compound in the presence of an essential combination of water and a methylenic ketone as a reaction activator. Kurtz lists typical starting methyl aromatic compounds as toluene, mon-xylene, p-xylene or mixtures thereof and discloses that the methyl aromatic compound should be present in an amount of 2 to 20, preferably 8 to 16, percent by weight of the fatty acid solvent—that is, at a solvent-to-methyl aromatic compound weight ratio of 5:1 to 50:1 or preferably 6.3:1 to 12.5:1. The resulting crude aromatic acid is purified by first heating it to 225°-260° C. and at at least autogenous pressure, then cooling it to below 170° C. to crystallize it and then, if desired, recrystallization.

Zimmerschied et al., U.S. Pat. No. 3,354,202, disclose a process for the liquid-phase oxidation of polymethylbenzenes to benzene carboxylic acids such as trimesic acid, in the presence of a catalyst comprising cobalt, manganese and bromine and at a volume ratio of solvent-to-starting material of 2:1 to 5:1.

Meyer et al., U.S. Pat. No. 3,261,846 disclose a method for making trimellitic acid by the liquid-phase oxidation of pseudocumene in a solvent and in the presence of catalyst comprising cobalt, manganese and bromine components. The only weight ratios of solvent-to-pseudocumene disclosed are 3:1 and 4:1 in column 5, lines 15-16 and column 7, lines 21-22. The method of Meyer et al. does not involve the addition of water to the separated solid trimelletic acid product.

OBJECTS OF THE INVENTION

It is therefore a general object of the present invention to provide an improved method which overcomes the aforesaid problems of prior art methods for producing higher quality trimesic acid by the liquid-phase oxidation of mesitylene with an oxygen-containing gas in a solvent and in the presence of an oxidation catalyst comprising cobalt-, manganese-, and bromine-containing components.

More particularly, it is an object of the present invention to provide a method for producing trimesic acid by the aforesaid liquid-phase oxidation of mesitylene which affords a high yield of trimesic acid product having reduced contents of colored and other organic and inorganic impurities and is easier to dry.

Other objects and advantages of the invention will become apparent upon reading the following detailed description and appended claims.

SUMMARY OF THE INVENTION

These objects are achieved by the method of this invention for producing purified trimesic acid comprising: oxidizing mesitylene with an oxygen-containing gas in the liquid phase in a solvent at an elevated temperature and pressure and in the presence of an oxidation catalyst comprising cobalt, manganese, and bromine components to form a product mixture comprising crude trimesic acid, wherein the solvent is a $C_2$-$C_6$ monocarboxylic acid, water or a mixture thereof and the weight ratio of solvent-to-mesitylene is in the range of from 5:1 to about 20:1; thereafter crystallizing the crude trimesic acid by cooling the product mixture to a temperature in the range of from about 80° C. to about 105° C.; separating the crystallized trimesic acid from the product mixture at a temperature in the range of from about 80° C. to about 105° C.; and washing the separated crude trimesic acid with water at a temperature in the range of from about 10° C. to about 100° C. and at a weight ratio of water-to-separated trimesic acid in the range of from about 0.5:1 to about 10:1 to form purified trimesic acid.

DETAILED DESCRIPTION OF THE PREFERRED EMBODIMENTS

Suitable solvents for use in the oxidation step of the method of this invention include any aliphatic $C_2$-$C_6$ monocarboxylic acid such as acetic acid, propionic acid, n-butyric acid, isobutyric acid, n-valeric acid, trimethylacetic acid, and caproic acid and water and mixtures thereof. Preferably, the solvent is a mixture of acetic acid and water, which more preferably contains from 1 to 20 weight percent of water, as introduced into the oxidation reactor. Since heat generated in the highly exothermic liquid-phase oxidation is dissipated at least partially by vaporization of solvent in the oxidation reactor, some of the solvent is withdrawn from the reactor as a vapor, which is then withdrawn from the oxidation reactor as a vent gas, condensed and recycled to the reactor.

The weight ratio of solvent-to-mesitylene fed to the oxidation step is from about 5:1 to about 20:1, and preferably from about 5:1 to about 15:1.

The source of molecular oxygen employed in the oxidation step of the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the gas-vapor mixture withdrawn from the reactor.

The catalyst employed in the oxidation step of the method of this invention comprises cobalt, manganese, and bromine components, and can additionally comprise accelerators known in the art. Preferably, the catalyst consists essentially of the cobalt-, manganese-, and bromine-containing components. The weight ratio of cobalt (calculated as elemental cobalt) in the cobalt component of the catalyst-to-mesitylene in the liquid-phase oxidation is in the range of from about 0.1 to about 10 milligram atoms (mga) per gram mole of mesitylene. The weight ratio of manganese (calculated as elemental manganese) in the manganese component of the catalyst-to-cobalt (calculated as elemental cobalt) in the cobalt component of the catalyst in the liquid-phase oxidation is in the range of from about 0.1 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.1 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromine can be employed. The 0.1:1.0 to 1.5:1.0 bromine-to-total cobalt and manganese milligram atom ratio is provided by a suitable source of bromine. Such bromine sources include elemental bromine ($Br_2$), or ionic bromide (e.g., HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.1:1.0 to 1.5:1.0. The bromine ion released from the organic bromides at the oxidation operating conditions can be readily determined by known analytical means. Tetrabromoethane, for example, at operating temperatures of 170° C. to 225° C. has been found to yield about 3 effective gram atoms of bromine per gram mole.

In operation, the minimum pressure at which the oxidation reactor is maintained is that pressure which will maintain a substantial liquid phase of the mesitylene and at least 70 percent of the solvent. The mesitylene and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/cm² to about 35 kg/cm², and typically are in the range of from about 10 kg/cm² to about 30 kg/cm². The temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

The oxidation can be performed either on a continuous or preferably semicontinuous basis. In the continuous mode, each of the mesitylene, air, solvent, and catalyst are continuously introduced into the reactor, and a product stream comprising trimesic acid and catalyst components dissolved in the solvent is withdrawn from the reactor. In the semicontinuous mode, the solvent and catalyst are initially introduced batchwise into the reactor and then mesitylene and air are continuously introduced into the reactor.

Thereafter, the product stream in the continuous mode or the reactor contents in the semicontinuous mode are cooled to a temperature in the range of from about 80° C. to about 105° C. in at least one step and in at least one crystallizer such that essentially all of the trimesic acid crystallizes in the solvent. Following crystallization, the resulting slurry of trimesic acid in the mother liquor is separated, typically by contrifugation, at a temperature in the range of from about 80° C. to about 105° C. Generally the separation is performed at essentially the same temperature as the crystallization.

The benefits of the aforesaid range of ratios of solvent-to-mesitylene for the oxidation stage in the method of this invention are illustrated in Tables 1 and 2 by the parameters and conditions employed in and the results from semi-continuous pilot plant oxidations of mesitylene in Runs 1-8. In Runs 1-8, the same oxidation reactor was precharged with solvent and catalyst, and then the reactor contents were preheated and prepressurized. When the initiation temperature and pressure were reached, the introductions of mesitylene and air into the reactor were commenced simultaneously. The rate of introduction of mesitylene was constant during the run, and the rate of introduction of air was adjusted during the run in order to maintain the concentration of oxygen in the vent gases leaving the reactor at a level of 2-6 volume percent. After the introduction of mesitylene was terminated and the oxidation reactor had proceeded to completion, the introduction of air was terminated. Then after the reactor was depressurized and cooled to 80-105° C. to crystallize the crude trimesic acid, the reactor contents were drained from the reactor and the crude trimesic acid was then separated from the liquor at 80-105° C. and finally washed with acetic acid at about 90° C. at a weight ratio of about 1 pound of acetic acid per pound of solids. The experimental parameters and conditions employed and results obtained in Runs 1-4 and Runs -8 are set forth in Tables 1 and 2, respectfully.

Except for the weight ratio of solvent-to-mesitylene, all conditions and parameters employed in

TABLE 1

| Parameters | Run 1 | Run 2 | Run 3 | Run 4 |
|---|---|---|---|---|
| Solvent-to-mesitylene weight ratio | 3.45 | 3.48 | 3.56 | 3.56 |
| Mesitylene fed to oxidation reactor | | | | |
| feed rate, lbs/hr | 4.0 | 4.1 | 2.0 | 2.0 |
| total mesitylene fed, lbs | 3.53 | 3.51 | 3.43 | 3.43 |
| Wt. of solvent in oxidation reactor | | | | |
| glacial acetic acid, lbs | 11.59 | 11.62 | 11.62 | 11.63 |
| water, lbs | 0.601 | 0.590 | 0.581 | 0.581 |
| total, lbs | 12.190 | 12.21 | 12.201 | 12.211 |
| Catalyst concentration, wt % | | | | |
| cobalt | 0.0240 | 0.0240 | 0.0256 | 0.0256 |
| manganese | 0.0440 | 0.0440 | 0.0426 | 0.0425 |
| bromine | 0.0918 | 0.0897 | 0.1111 | 0.1106 |
| Total wt % of solvent and catalyst, lbs | 12.24 | 12.27 | 12.25 | 12.26 |
| Reaction temperature, °C. | 220 | 220 | 220 | 220 |
| Reaction pressure, psig | 300 | 300 | 300 | 300 |
| Air flow rate, SCFH[1] | 300 | 340 | 175 | 170 |
| Air flow time, minutes | 53.8 | 52.2 | 124.0 | 124.1 |
| Vent oxygen concentration, vol % | 4.0 | 4.0 | 3.0 | 4.0 |
| Results | | | | |
| Trimesic acid yield, mole % | 55.9 | 61.2 | 63.6 | 69.2 |
| Trimesic acid and mother liquor color characteristics | tan solids, brown liquor | tan solids, light brown liquor | light tan solids, light brown liquor | light tan solids, light brown liquor |
| Optical density of final trimesic acid | 1.62 | — | 1.03 | 0.82 |
| Acid number[2] | 772 | — | 788 | 784 |

Footnotes
[1] Standard cubic feet per hour, measured at 0° C. and 1 atmosphere pressure absolute.
[2] Milligrams of KOH per gram of cake.

TABLE 2

| Parameters | Run 5 | Run 6 | Run 7 | Run 8 |
|---|---|---|---|---|
| Solvent-to-mesitylene weight ratio | 4.98 | 5.07 | 4.99 | 4.98 |
| Mesitylene fed to oxidation reactor | | | | |
| feed rate, lbs/hr | 3.2 | 3.0 | 2.9 | 3.0 |
| total mesitylene fed, lbs | 2.70 | 2.65 | 2.70 | 2.70 |
| Weight of solvent in oxidation reactor | | | | |
| glacial acetic acid, lbs | 12.80 | 12.79 | 12.78 | 12.78 |
| water, lbs | 0.649 | 0.647 | 0.666 | 0.662 |
| total, lbs | 13.449 | 13.437 | 13.446 | 13.442 |
| Catalyst concentration, wt % | | | | |
| cobalt | 0.0250 | 0.0251 | 0.0251 | 0.0250 |
| manganese | 0.0460 | 0.0447 | 0.0441 | 0.0440 |
| bromine | 0.1076 | 0.1095 | 0.1122 | 0.1099 |
| Total wt % of solvent and catalyst, lbs | 13.52 | 13.51 | 13.50 | 13.50 |
| Reaction temperature, °C. | 220 | 220 | 220 | 220 |
| Reaction pressure, psig | 300 | 300 | 300 | 300 |
| Air flow rate, SCFH[1] | 270 | 270 | 265 | 265 |
| Air flow time, minutes | 60.5 | 60.8 | 63.7 | 62.4 |
| Vent oxygen concentration, vol % | 4.0 | 4.0 | 4.0 | 3.0 |
| Results | | | | |
| Trimesic acid yield, mole % | 87.9 | 86.5 | 86.3 | 88.2 |
| Trimesic acid and mother liquor color characteristics | white solids light lemon liquor | | | |
| Optical density of final trimesic acid | — | 0.57 | 0.53 | 0.54 |
| Acid Number[2] | 798 | 798 | 798 | 796 |

Footnotes
[1] Standard cubic feet per hour measured at 0° C. and 1 atmosphere pressure absolute.
[2] Milligrams of KOH per gram of cake.

Runs 1-8 were held substantially constant. In Runs 1-4, the weight ratios of solvent-to-mesitylene were in the range of 3.45-3.56, which are typical for liquid phase oxidations of alkyl aromatics using cobalt-manganese-bromine catalysts. In Runs 5-8, the weight ratios of solvent-to-mesitylene were in the range of 4.98-5.07, that is, at least about 5:1. The yields and acid numbers of the trimesic acid products are substantially greater and the color characteristics including optical densities, of the trimesic acid products are substantially better in Runs 5-8 relative to those from Runs 1-4. In general, Runs 1-4 demonstrated typical symptoms of catalyst deactivation, and the oxidations were difficult to control, necessitating wide variations in the air flow rate in order to maintain the desired vent oxygen concentration. By contrast, Runs 5-8 showed no evidence of catalyst deactivation, and the oxidations proceeded smoothly to produce visibly whiter product and in higher yield.

The benefits of the aforesaid temperature range for both the crystallization and separation of trimesic acid in the method of this invention are illustrated by the results in Table 3 of analyses of purified trimesic acid samples produced using the same oxidation conditions, which conditions are within the ranges therefor described hereinabove. The samples analyzed had been washed with acetic acid after being separated.

The organic impurities tested in Table 3 constitute at least 80 weight percent of the total organic impurities in purified trimesic acid produced in accordance with the oxidation conditions of the method of this invention. The optical densities reported in Tables 1-4 herein were obtained by measurement of the absorbance of a 2 weight percent solution of trimesic acid in aqueous ammonium hydroxide at a frequency of 320 nanometers.

The results in Table 3, illustrate clearly that a purified trimesic acid product having substantially lower levels of organic impurities and improved optical density is obtained when the trimesic acid is crystallized and filtered at a temperature in the range of from about 80° C. to about 105° C.

As illustrated hereinbelow in Table 3, even if the crystallization and separation are performed under the conditions therefor of the method of this invention, after separation of the mother liquor, the resulting trimesic acid contains undesirable inorganic and organic impurities. However, I have found that the concentrations in trimesic acid of both organic and inorganic impurities, but particularly of the inorganic metal impurities, are reduced substantially by washing the filter cake with water. Although a water wash is ineffective in removing either organic or inorganic impurities from terephthalic acid and naphthalene-2,6-dicarboxylic acid, a water wash is very effective in removing organic and inorganic impurities from trimesic acid and, in fact, as indicated by the data in Table 4 hereinbelow, is much more effective than an acetic acid wash in the removal of organic and inorganic impurities from trimesic acid and in improving the color characteristics of trimesic acid.

TABLE 3

| | Concentration (parts per million by weight) in Trimesic Acid Crystallized and Separated at | |
|---|---|---|
| Impurities | 24° C. | 104° C. |
| cobalt | 132 | 117 |
| manganese | 376 | 389 |
| bromine | 158 | 125 |
| trimellitic anhydride | 107 | 85 |
| terephthalic acid | 429 | 73 |
| isophthalic acid | 2525 | 1002 |
| benzoic acid | 987 | 911 |
| 5-methylisophthalic acid | 4001 | 911 |
| tetracarboxybenzene | 1482 | 1289 |
| dicarboxybenzaldehyde | 356 | 146 |
| Properties | | |
| acid number | 778 | 789 |
| optical density | 1.93 | 1.39 |

TABLE 4

| | Concentration[1] in Trimesic Acid[2] | | | |
|---|---|---|---|---|
| | Without | Acetic | Water Wash | |
| Impurity | Wash[3] | Acid Wash[4] | A[5] | B[6] |
| trimellitic anhydride | 205 | 46 | 31 | 37 |
| terephthalic acid | 176 | 94 | 60 | 66 |
| isophthalic acid | 1633 | 475 | 386 | 400 |
| 5-methylisophthalic acid | 1407 | 609 | 321 | 338 |
| 3,5-dimethylbenzoic acid | 78 | 38 | 34 | 39 |
| cobalt | 290 | 268 | 22 | 35 |
| manganese | 442 | 357 | 50 | 51 |
| bromine | 207 | 97 | 81 | 78 |
| Properties | | | | |
| optical density | 1.33 | 0.71 | 0.68 | 0.68 |
| color | pink | pink | white | white |

Footnotes:
[1]Parts per million by weight
[2]Obtained by crystallization and separation, each at 93° C.
[3]Typical values for trimesic acid prepared under similar oxidation conditions and then crystallized and separated at 90° C.
[4]At 93° C. with 1 part of acetic acid per 1 part of filter cake by weight
[5]At 66° C. with 1 part of water per 1 part of filter cake by weight
[6]At 10° C. with 1.2 parts of water per 1 part of filter cake by weight The washed samples of trimesic acid were prepared in the same oxidation run and using oxidation conditions within the ranges therefor described hereinabove for the method of this invention. The organic impurities listed in Table 4 constitute at least 80 weight percent of the total organic impurities in trimesic acid produced in accordance with the oxidation conditions of the method of this invention.

The water wash step of the method of this invention is performed at a temperature in the range of from about 10° C., preferably from about 25° C., to about 100° C., preferably to about 50° C., and a weight ratio of water-to-trimesic acid filter cake in the range of from about 0.5:1, preferably from about 1:1, to about 10:1, preferably to about 1.5:1. The water wash is performed for a time in the range of from about 0.5 minute to about 5 minutes.

The resulting purified trimesic acid contains less than 0.5%, preferably less than 0.1%, of total organic impurities and less than 0.05%, preferably less than 0.02% of total inorganic impurities, based on the weight of the trimesic acid.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:
I claim:

1. A method for producing trimesic acid comprising: oxidizing mesitylene with an oxygen-containing gas in the liquid phase in a solvent at an elevated temperature and pressure and in the presence of an oxidation catalyst comprising cobalt, manganese, and bromine components to form a product mixture comprising crude trimesic acid, wherein the solvent is a $C_2$-$C_6$ monocarboxylic acid, water or a mixture thereof and the volume ratio of solvent-to-mesitylene is in the range of from about 5:1 to about 20:1; thereafter crystallizing the crude trimesic acid by cooling the product mixture to a temperature in the range of from about 80° C. to about 105° C.; separating the crystallized trimesic acid from the product mixture at a temperature in the range of from about 80° C. to about 105° C.; and washing the separated crude trimesic acid with water at a temperature in the range of from about 10° C. to about 100° C. and at a weight ratio of water to separated trimesic acid in range of from about 0.5:1 to about 10:1 to form purified trimesic acid.

2. The method of claim 1 wherein the volume ratio of solvent-to-mesitylene in the oxidation step is from about 5:1 to about 15:1.

3. The method of claim 1 wherein the solvent in the oxidation step is a mixture of acetic acid and water containing from 1 to 20 weight percent of water.

4. The method of claim 1 wherein the oxidation step is performed at a temperature in the range of from about 120° C. to about 240° C.

5. The method of claim 1 wherein the oxidation step is performed at a gauge pressure in the range of from about 0 to about 35 kg/cm$^2$.

6. The method of claim 1 wherein the weight ratio of cobalt calculated as elemental cobalt, in the cobalt component of the catalyst-to-mesitylene in the liquid phase oxidation is in the range of from about 0.1 to about 10 mga per gram mole of mesitylene, the weight ratio of manganese, calculated as elemental manganese, in the manganese component of the catalyst-to-cobalt, calculated as elemental cobalt, in the cobalt component of the catalyst is in the range of from about 0.1 to about 10 mga per mga of cobalt, and the weight ratio of bromine, calculated as elemental bromine, in the bromine component of the catalyst-to-total cobalt and manganese, calculated as elemental cobalt and elemental manganese, in the cobalt and manganese components of the catalyst is in the range of from about 0.1 to about 1.5 mga per mga of total cobalt and manganese.

7. The method of claim 1 wherein air is the oxygen-containing gas.

8. The method of claim 1 wherein the separated crude trimesic acid is washed with water at a temperature in the range of from about 25° C. to about 50° C.

9. The method of claim 1 wherein the separated crude trimesic acid is washed with water at a weight ratio of water-to-separated trimesic acid in the range of from about 1:1 to about 1.5:1.

* * * * *

UNITED STATES PATENT AND TRADEMARK OFFICE
CERTIFICATE OF CORRECTION

PATENT NO. : 5,107,020
DATED : April 21, 1992
INVENTOR(S) : Aubrey C. Reeve

It is certified that error appears in the above-indentified patent and that said Letters Patent is hereby corrected as shown below:

Column 5, line 26, "Runs -8 are" should read --Runs 5-8 are--

Signed and Sealed this

Fifteenth Day of June, 1993

Attest:

MICHAEL K. KIRK

Attesting Officer     Acting Commissioner of Patents and Trademarks